United States Patent
Samulski

(10) Patent No.: US 6,904,323 B2
(45) Date of Patent: Jun. 7, 2005

(54) NON-INVASIVE APPARATUS AND METHOD FOR PROVIDING RF ENERGY-INDUCED LOCALIZED HYPERTHERMIA

(75) Inventor: Thaddeus V. Samulski, Chapel Hill, NC (US)

(73) Assignee: Duke University, Durham, NC (US)

( * ) Notice: Subject to any disclaimer, the term of this patent is extended or adjusted under 35 U.S.C. 154(b) by 34 days.

(21) Appl. No.: 10/437,838

(22) Filed: May 14, 2003

(65) Prior Publication Data

US 2004/0230263 A1 Nov. 18, 2004

(51) Int. Cl.[7] .................................................. A61F 2/00
(52) U.S. Cl. ...................................... 607/101; 607/154
(58) Field of Search ............................. 607/96, 98, 99, 607/101, 102, 154

(56) References Cited

U.S. PATENT DOCUMENTS

| | | | | |
|---|---|---|---|---|
| 4,397,314 A | * | 8/1983 | Vaguine | 607/104 |
| 4,586,516 A | * | 5/1986 | Turner | 607/154 |
| 5,097,844 A | * | 3/1992 | Turner | 607/156 |
| 5,231,997 A | * | 8/1993 | Kikuchi et al. | 607/154 |
| 5,540,737 A | | 7/1996 | Fenn | |
| 5,928,159 A | | 7/1999 | Eggers et al. | |
| 6,275,738 B1 | | 8/2001 | Kasevich et al. | |
| 6,347,251 B1 | * | 2/2002 | Deng | 607/101 |
| 6,358,246 B1 | | 3/2002 | Behl et al. | |
| 6,391,026 B1 | | 5/2002 | Hung et al. | |
| 6,425,912 B1 | * | 7/2002 | Knowlton | 607/101 |
| 6,468,273 B1 | | 10/2002 | Leveen et al. | |

* cited by examiner

Primary Examiner—Roy D. Gibson
(74) Attorney, Agent, or Firm—Jenkins, Wilson & Taylor, P.A.

(57) ABSTRACT

An apparatus for providing hyperthermia treatment for enhancing cancer therapy includes an applicator body and a plurality of antennas operatively associated with the applicator body. The applicator body has a concave profile extending from an aperture and defines an open cavity for receiving RF standing waves. The antennas are arrayed for transmitting RF standing waves at respective selected amplitudes and relative phases into the cavity and generally toward a tumor-containing tissue disposed in operative alignment with the antennas. In use, the tissue such as a breast or chest wall is immersed in the cavity or supported on a pillow mounted to the cavity. The cavity contains a fluid such as deionized water through which the RF energy is transmitted to heat the tissue. The hyperthermia treatment can be used to enhance the effects of a cancer-related therapy such as radiotherapy or chemotherapy.

61 Claims, 7 Drawing Sheets

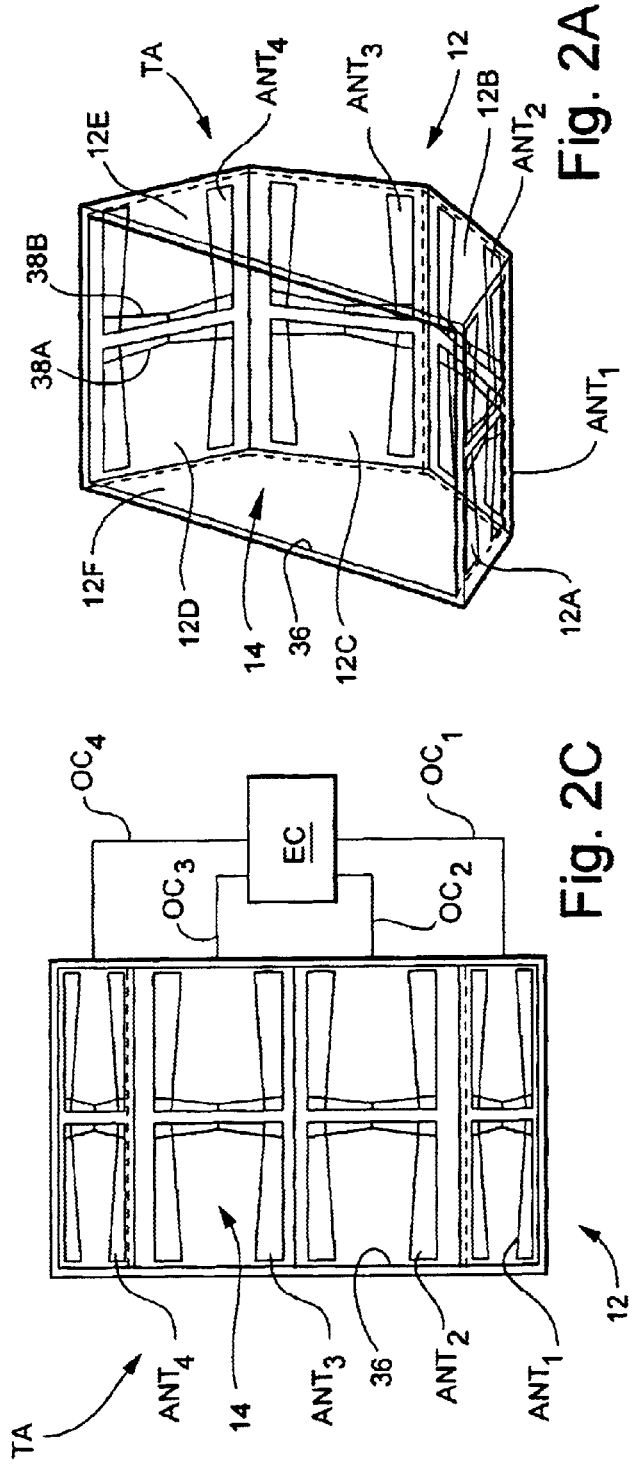
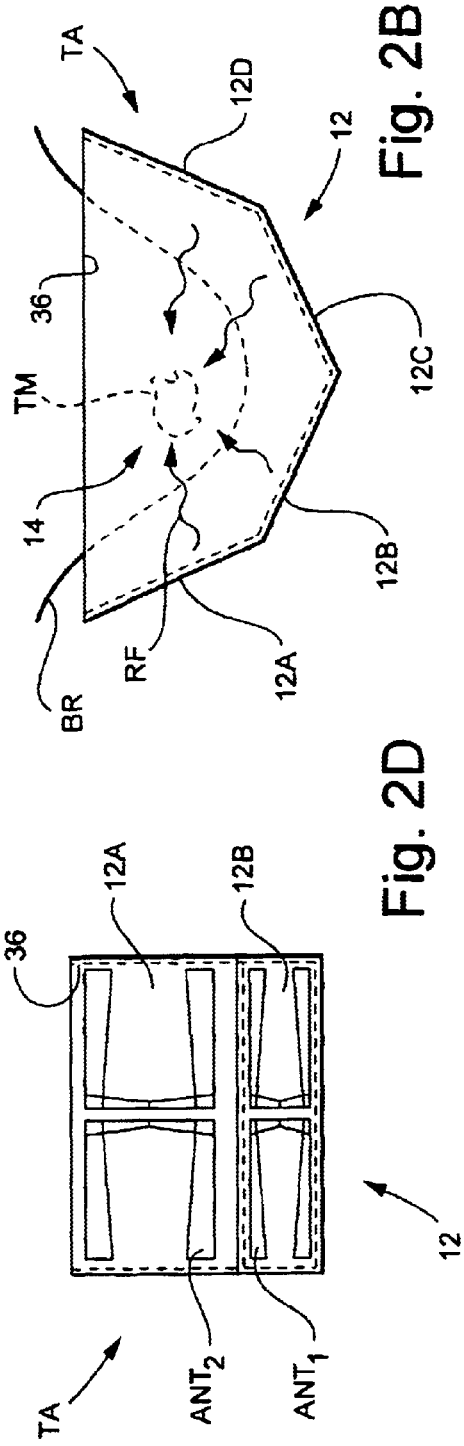
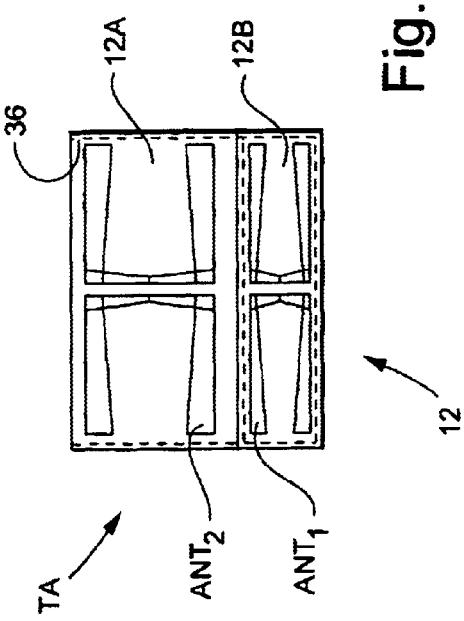

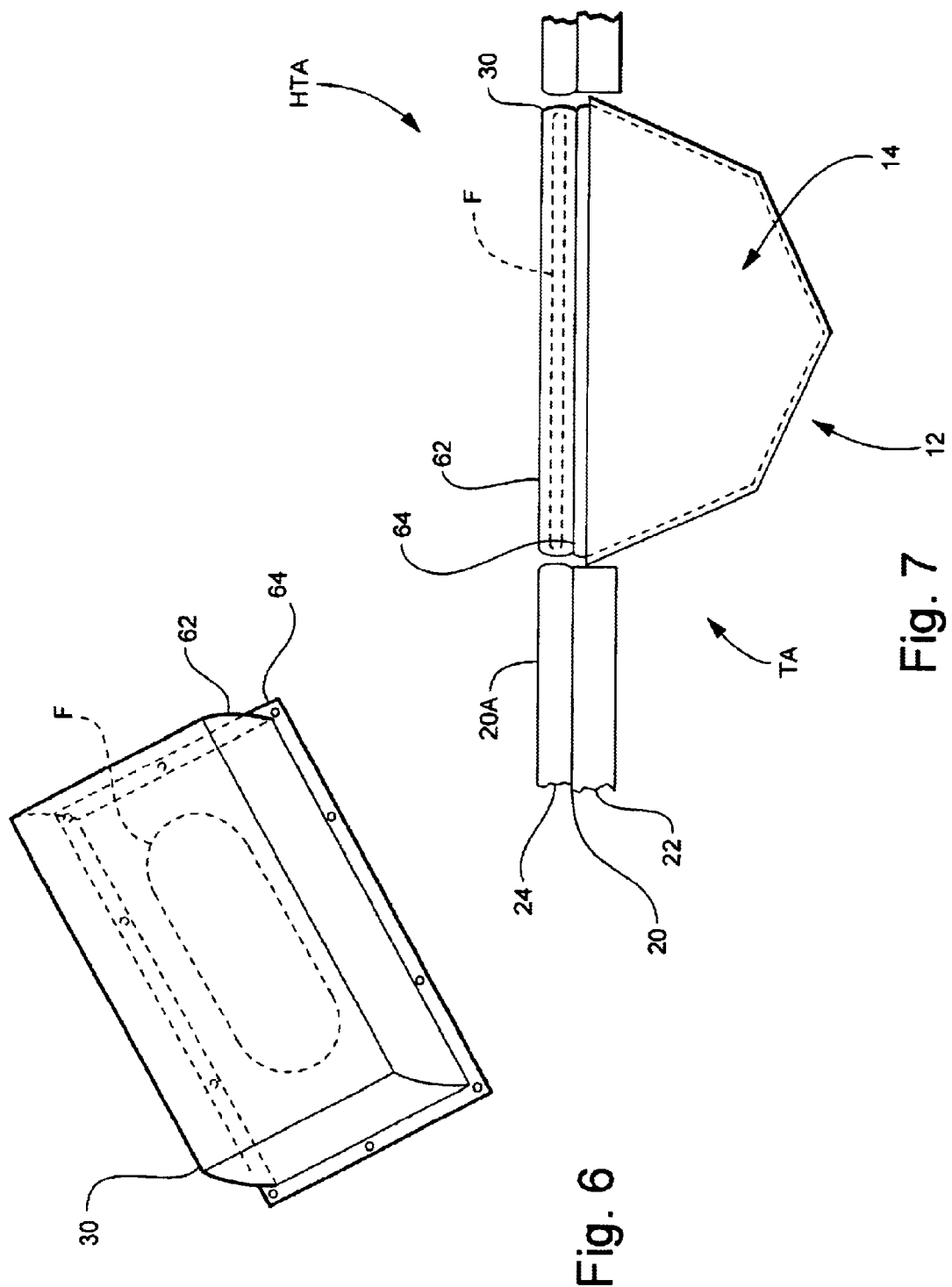

NON-INVASIVE APPARATUS AND METHOD FOR PROVIDING RF ENERGY-INDUCED LOCALIZED HYPERTHERMIA

GOVERNMENT INTEREST

This invention was made with Government support under Grant No. 5P01 CA 427 45-16 awarded by the National Institutes of Health. The Government has certain rights in the invention.

TECHNICAL FIELD

The present invention generally relates to inducing hyperthermia in a desired target such as living tissue. More particularly, the present invention relates to non-invasively causing localized hyperthermia in tissue such as tumor-containing tissue using a phased antenna array to direct standing waves of RF energy to the tissue. An advantageous application of the present invention is enhancing the effects of cancer-related therapeutic procedures.

BACKGROUND ART

Certain types of cancers such as breast cancers, particularly inflammatory and locally advanced tumors, often resist traditional treatments. It has been statistically shown that sixty to seventy percent of victims of such breast tumors do not survive past five years. The efficacy of conventional methods of treating cancer, such as radiotherapy and chemotherapy, is limited due to necessary constraints on dosage amounts for safety. For example, it is known that chemotherapy can be applied in sufficient amounts to kill virtually all cancer cells of a tumor. However, the amounts of chemotherapy needed to achieve this can be high enough to cause poisoning of the patient and/or undue side effects. As another example, the intensity of an x-ray beam applied in accordance with radiotherapy cannot be so high as to damage nearby critical organs and surrounding healthy tissues. Accordingly, there is an ongoing need to develop techniques that enhance existing cancer-related therapeutic procedures so as to increase their effectiveness without increasing the risk of damage to healthy tissue and causing additional discomfort for cancer patients.

One recent approach toward improving cancer therapy is to subject a tumor to a hyperthermia treatment. The application of heat to cancer cells has been found to increase the efficacy of certain types of therapies for various proposed reasons. Microwave and radio frequency (RF) energy sources have been employed to conduct hyperthermia treatment. Microwave energy has been applied to tumors using waveguides. However, the relatively high frequencies at which microwaves propagate are not suitable for deep penetration into tissue. RF energy has also been utilized in some instances, and has the potential to achieve greater penetration due to relatively lower frequencies. However, both microwave and RF techniques have in the past required the use of invasive elements, such as wires, catheters, lumens, probes, receivers, and the like. These invasive elements are typically inserted or embedded in the tumor to be treated to ensure proper coupling and focusing of the electromagnetic energy at the tumor site. The use of invasive elements adds complexity to the procedure and is a source of discomfort for patients. Examples of invasive heating techniques using microwave and RF energy are disclosed in U.S. Pat. Nos. 5,928,159; 6,275,738; 6,358,246; 6,391,026; and 6,468,273.

It therefore would be desirable to provide a method and apparatus for non-invasively inducing hyperthermia in a tumor by applying electromagnetic energy, and preferably RF energy, to the tumor in a controllable, coherent manner, and while avoiding or reducing problems associated with conventional techniques.

SUMMARY OF THE INVENTION

According to one embodiment, an apparatus for providing hyperthermia treatment for enhancing cancer therapy comprises an applicator body and a plurality of antennas. The applicator body has a concave profile extending from an aperture, and defines an open cavity for receiving RF standing waves. The antennas are operatively associated with the applicator body and are arrayed for transmitting RF standing waves at respective selected amplitudes and relative phases into the cavity and generally toward a tumor-containing tissue disposed in operative alignment with the antennas.

According to another embodiment, a method for providing hyperthermia treatment for enhancing cancer therapy comprises the following steps. A tumor-containing tissue is placed in operative alignment with a phased array of antennas operatively associated with a body defining a cavity containing a fluid. RF energy is transmitted from the antennas through the fluid and to the tissue to heat the tissue.

According to yet another embodiment, a method for providing hyperthermia treatment to enhance tumor-related therapy comprises the following steps. A tumor-containing tissue is treated by performing a tumor-related therapeutical procedure. The tissue is placed in operative alignment with a phased array of antennas operatively associated with a body defining a cavity containing a fluid. RF energy is transmitted from the antennas, through the fluid, and into the tissue to heat the tissue.

It is therefore an object to provide an apparatus and method for inducing localized hyperthermia by applying controlled RF energy.

An object having been stated hereinabove, and which is addressed in whole or in part by the present invention, other objects will become evident as the description proceeds when taken in connection with the accompanying drawings as best described hereinbelow.

BRIEF DESCRIPTION OF THE DRAWINGS

FIG. 2A is a perspective view of a treatment applicator provided with the hyperthermia treatment apparatus according to one embodiment disclosed herein;

FIG. 2B is a side elevation view of the treatment applicator illustrated in FIG. 2A;

FIG. 2C is a top plan view of the treatment applicator illustrated in FIG. 2A;

FIG. 2D is a front elevation view of the treatment applicator illustrated in FIG. 2A;

FIG. 6 is a perspective view of a tissue support structure provided according to still another embodiment disclosed herein;

FIG. 7 is a partial side elevation view of a hyperthermia treatment apparatus including the treatment applicator illustrated in FIG. 2B and the tissue support structure illustrated in FIG. 6, both of which are mounted in a patient support structure provided therewith.

DETAILED DESCRIPTION OF THE INVENTION

Figure 1A:
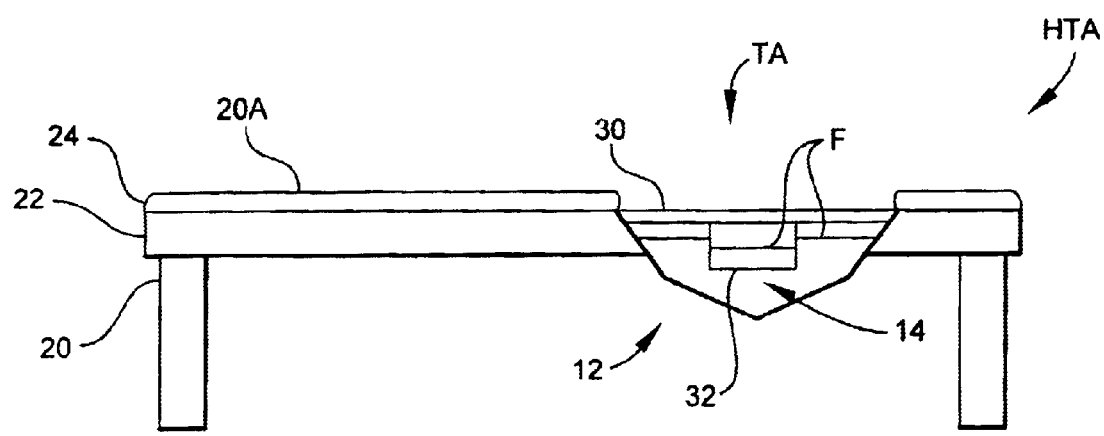
FIG. 1A is a side elevation view of a hyperthermia treatment apparatus according to an embodiment disclosed herein.
Figure 1B:
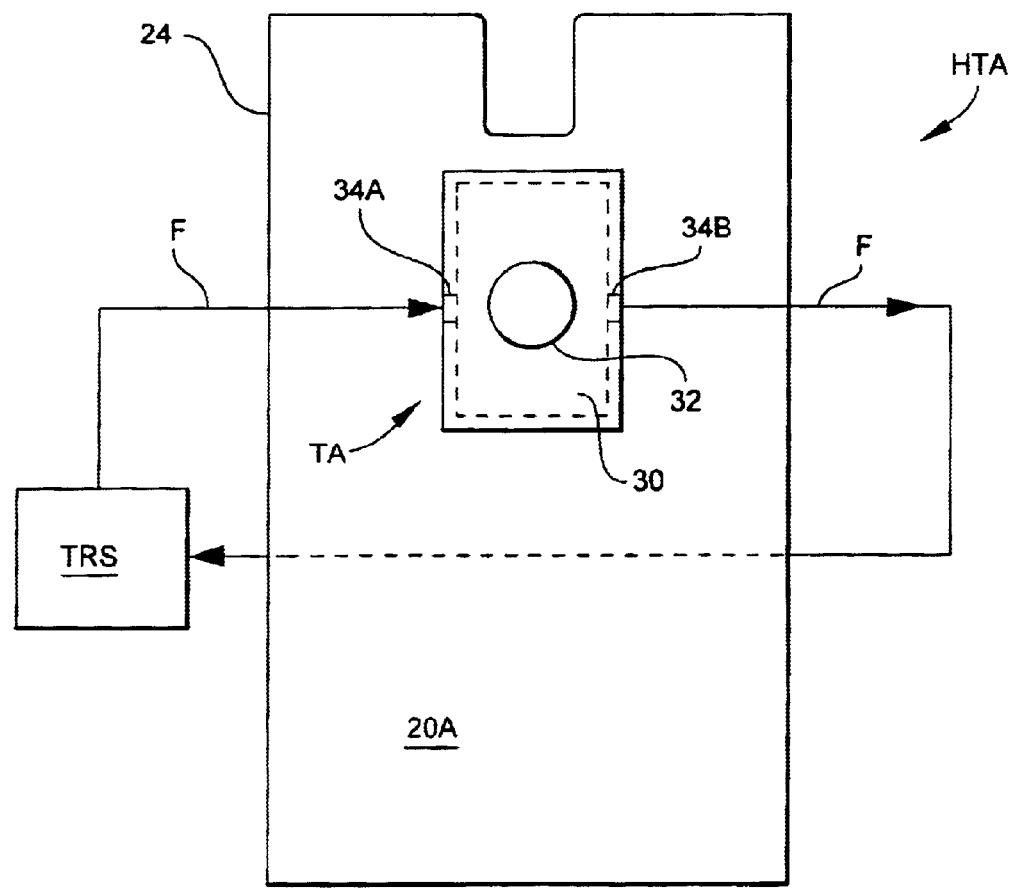
FIG. 1B is a top plan view of the hyperthermia treatment apparatus illustrated in FIG. 1A.

Referring now to FIGS. 1A and 1B, a hyperthermia treatment apparatus, generally designated HTA, is illustrated according to one embodiment. Hyperthermia treatment apparatus HTA primarily comprises a treatment applicator, generally designated TA, and associated electrical circuitry, generally designated EC (see FIGS. 2C and 8, described in detail hereinbelow). Treatment applicator TA has a body, generally designated 12, constructed to form an open cavity 14 with which a biological target such as tumor-afflicted tissue can be proximally disposed for exposure to RF electromagnetic energy via electromagnetic coupling. In one embodiment, body 12 is constructed from a clear polymeric material such as LEXAN® material. The profile of body 12 can be polygonal as illustrated or can be generally semi-spherical or semi-ovoid. The embodiments of hyperthermia treatment apparatus HTA illustrated herein are particularly advantageous for the treatment of tumors of the breast and chest wall. For this purpose, treatment applicator TA can be mounted in a cut-out section of any suitable patient support structure 20 (e.g., a table, bed or couch) such that its cavity 14 opens upwards toward a top surface 20A of patient support structure 20. In one embodiment, patient support structure 20 includes a base 22 and a padding 24. By this configuration, a patient can lie comfortably in a prone position on top surface 20A with the breast or chest wall to be treated depending or facing downwardly into cavity 14.

In some embodiments, hyperthermia treatment apparatus HTA further includes a tissue (e.g., breast or chest wall) support structure 30 that is secured to the top of treatment applicator TA by any suitable fastening means (not shown) such as threaded screws, bolts and nuts, or clamps. In FIGS. 1A and 1B, tissue support structure 30 includes a container 32 that extends into cavity 14 to provide additional support for a breast. The use of tissue support structure 30 will generally depend on breast size. Moreover, while container 32 is illustrated as being cup- or bowl-shaped, the size and shape of container 32 can generally depend on breast size and shape.

As further shown in FIGS. 1A and 1B, during the operation of hyperthermia treatment apparatus HTA according to advantageous embodiments, cavity 14 of treatment applicator TA and container 32 of tissue support structure 30 (when used) are filled with a suitable fluid F such as deionized water. The breast or other tissue can be immersed in fluid F during treatment. As shown in FIG. 1B, the temperature of fluid F can be regulated to prevent skin burns and improve patient comfort, by circulating fluid F through an inlet 34A and outlet 34B of cavity 14 as generally indicated by arrows and distributing the heat evenly around the tissue. The arrows in FIG. 1B can represent fluid flow through liquid conduits that communicate with any suitable temperature regulating system TRS. Water is useful as fluid F because its dielectric constant is similar to that of the tissue of a patient, and thus RF energy can be efficiently propagated and directed by treatment applicator TA (in a manner described hereinbelow) with minimal reflected energy. The use of water as fluid F is considered superior to air, at least in part because air cannot transfer heat as efficiently and its dielectric constant differs from water by a factor of about 10.

Referring now to FIGS. 2A–2D, details of treatment applicator TA are illustrated according to a four-antenna embodiment. Body 12 of treatment applicator TA includes six body sections or walls defining cavity 14. In the illustrated example, the body 12 sections include two opposing side sections 12E and 12F generally perpendicular to the plane of an aperture 36 of body 12; two opposing side sections 12A and 12D angled relative to aperture 36; and two angled bottom sections 12B and 12C. Aperture 36 is formed by the respective top edges of perpendicular side sections 12E and 12F and angled side sections 12A and 12D. Antennas $ANT_1$–$ANT_4$ are respectively disposed in each of angled side sections 12A and 12D and angled bottom sections 12B and 12C, although more or less antennas could be provided in angled side sections 12A and 12D and angled bottom sections 12B and 12C. Antennas $ANT_1$–$ANT_4$ can be secured to body 12 in any suitable manner, such as by gluing antennas $ANT_1$–$ANT_4$ to the inside surfaces of angled side sections 12A and 12D and angled bottom sections 12B and 12C. Antennas $ANT_1$–$ANT_4$ can have any design suitable for transmitting RF energy through a selected fluid such as water. In the advantageous embodiments illustrated herein, each antenna $ANT_1$–$ANT_4$ has a "bowtie" or "H" shape constructed from a pair of generally C-shaped antenna elements 38A and 38B. For each pair, antenna elements 38A and 38B (FIG. 2C) are inverted with respect to each other, with their corresponding legs opening away from each other. Antennas $ANT_1$–$ANT_4$ are arrayed along angled side sections 12A and 12D and angled bottom sections 12B and 12C to enable standing RF waves to be coherently focused toward the tissue residing in or over cavity 14. FIG. 2B schematically depicts a coherent pattern of standing RF waves RF focused on a tumor mass TM of a breast BR. As shown in FIG. 2C, each antenna $ANT_1$–$ANT_4$ communicates with electrical circuitry EC via respective low-loss output cables $OC_1$–$OC_4$ to provide RF energy as described hereinbelow.

Figure 3:
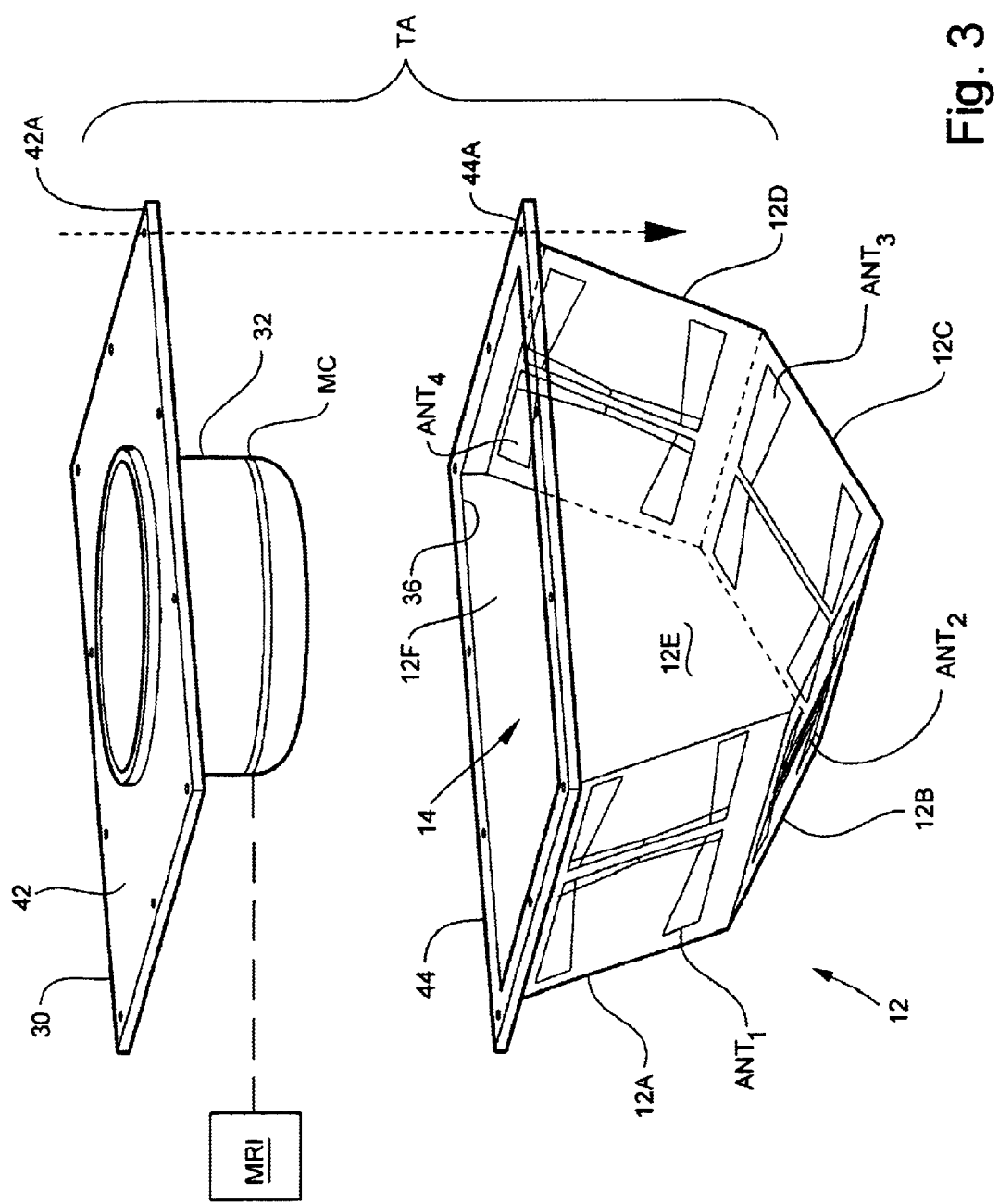
FIG. 3 is an exploded perspective view of the treatment applicator illustrated in FIG. 2A and a tissue support structure provided therewith according to one embodiment disclosed herein.

Referring now to FIG. 3, tissue support structure 30 includes a plate 42 from which container 32 extends downwardly. Plate 42 is sized to cover cavity 14 and thus enable tissue support structure 30 to be mounted onto body 12, for example at a rim 44 thereof. Tissue support structure 30 can be secured to body 12 by any suitable means, one example being the use of screws (not shown) tapped through respective apertures 42A and 44A of plate 42 and rim 44, or bolts extending through apertures 42A and 44A and held by nuts.

As further shown in FIG. 3, in some embodiments, a magnetic coil device MC can be mounted to the inside or outside of container 32 so as to circumscribe the breast or other tissue to be treated. Magnetic coil device MC can be coupled to any suitable magnetic resonance imaging (MRI) device MRI to generate images of the tumor in the breast during treatment. Apart from other known visual uses, the MRI images can be correlated to temperature, and hence magnetic coil device MC can be used as a temperature-sensing device. In other embodiments, a temperature-sensing device can be provided in the form of a thermometer that is physically inserted into the breast, such as through a catheter as is understood by persons skilled in the art. The use of magnetic coil device MC, however, is non-invasive and much less discomforting for the patient undergoing treatment.

Figure 4:
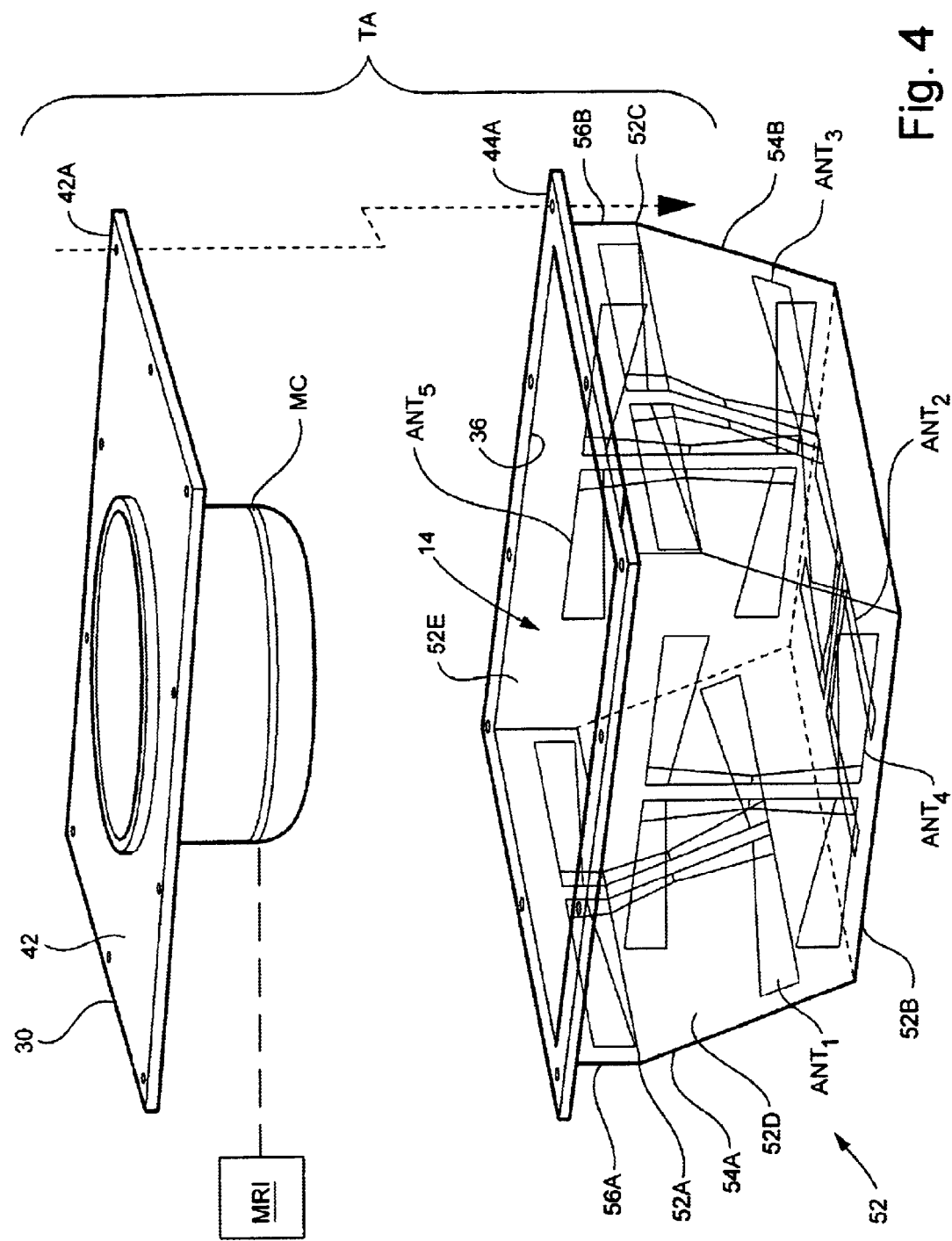
FIG. 4 is an exploded perspective view of a treatment applicator provided according to another embodiment disclosed herein, and a tissue support structure provided therewith.

Referring now to FIG. 4, treatment applicator TA is illustrated according to a five-antenna embodiment. Body 52 of treatment applicator TA includes five body sections or walls 52A–52E defining cavity 14. In the illustrated example, the body 12 sections include two opposing side sections 52D and 52E generally perpendicular to the plane of aperture 36 of body 52; two opposing side sections 52A and 52C angled relative to aperture 36; and a bottom section 52B generally parallel with aperture 36. Antennas $ANT_1$–$ANT_5$ are respectively disposed in angled side section 52A, bottom section 52B, angled side section 52C, perpendicular side section 52D, and perpendicular side section 52E, although more or less antennas could be provided in each section 52A–52E. Antennas $ANT_1$–$ANT_5$ can be secured to body 52 in any suitable manner, and can have any design, such as described hereinabove with reference to FIGS. 2A–2D and 3. In the embodiment illustrated in FIG. 4, side sections 52A and 52C include both angled portions 54A, 56A and perpendicular portions 54B, 56B, respectively, and their corresponding antennas $ANT_1$ and $ANT_3$ disposed over both portions 54A, 56A and 54B, 56B, to provide additional directions over which standing RF waves propagate toward the tissue residing in cavity 14.

Figure 5:
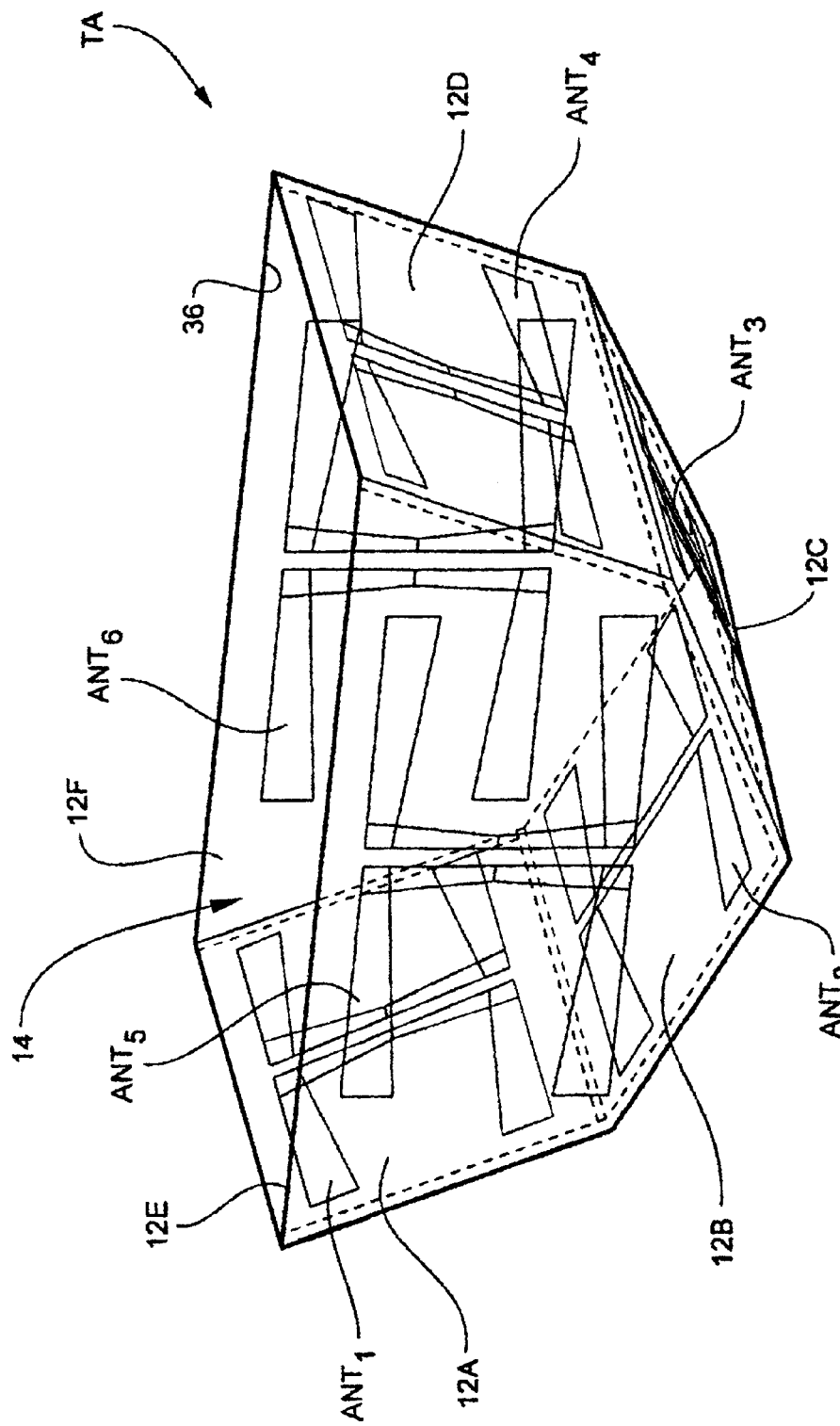
FIG. 5 is a perspective view of a treatment applicator provided according to yet another embodiment disclosed herein.

Referring now to FIG. 5, treatment applicator TA is illustrated according to a six-antenna embodiment. Body 12 of treatment applicator TA is similar to that shown in FIGS. 2A–2D and 3. In FIG. 5, however, two additional antennas $ANT_5$ and $ANT_6$ are provided and are mounted at perpendicular side sections 12E and 12F, respectively. Antennas $ANT_1$–$ANT_6$ can be secured to body 12 in any suitable manner, and can have any design, such as the bowtie shape described hereinabove with reference to FIGS. 2A–2D.

For a given hyperthermia treatment, the selection of the four-, five- or six-antenna embodiment of treatment applicator TA can depend on factors including the type of tissue to be treated, such as the size and/or shape of a breast; the type, location and advancement of the tumor to be treated; and the pattern of standing RF waves determined to be optimal for the treatment of a given tumor. The decision to employ tissue support structure 30 with treatment applicator TA can also depend on these factors. For instance, the use of the four-antenna embodiment of treatment applicator TA without tissue support structure 30 can be indicated for a large-size breast afflicted with a bilateral disease.

Referring now to FIGS. 6 and 7, an alternate embodiment of treatment applicator TA is illustrated in which tissue support structure 30 is provided in the form of a pillow 62 filled with a suitable fluid F such as deionized water and attached to a planar structure such as a silastic membrane 64. Similar to plate 42 of tissue support structure 30 illustrated in FIGS. 1A, 1B, 3 and 4, membrane 64 is sized to cover cavity 14 and enable pillow 62 to be mounted onto body 12 of treatment applicator TA. As shown in FIG. 7, pillow 62 is sized to be generally flush with top surface 20A of patient support structure 30. Pillow 62 is useful for treating superficial or skin diseases, and post-mastectomy chest wall recurrence. The patient can be comfortably positioned prone on patient support structure 20, with the chest wall lying on pillow 62 in operative alignment with antennas ANT of treatment applicator TA.

Figure 8:
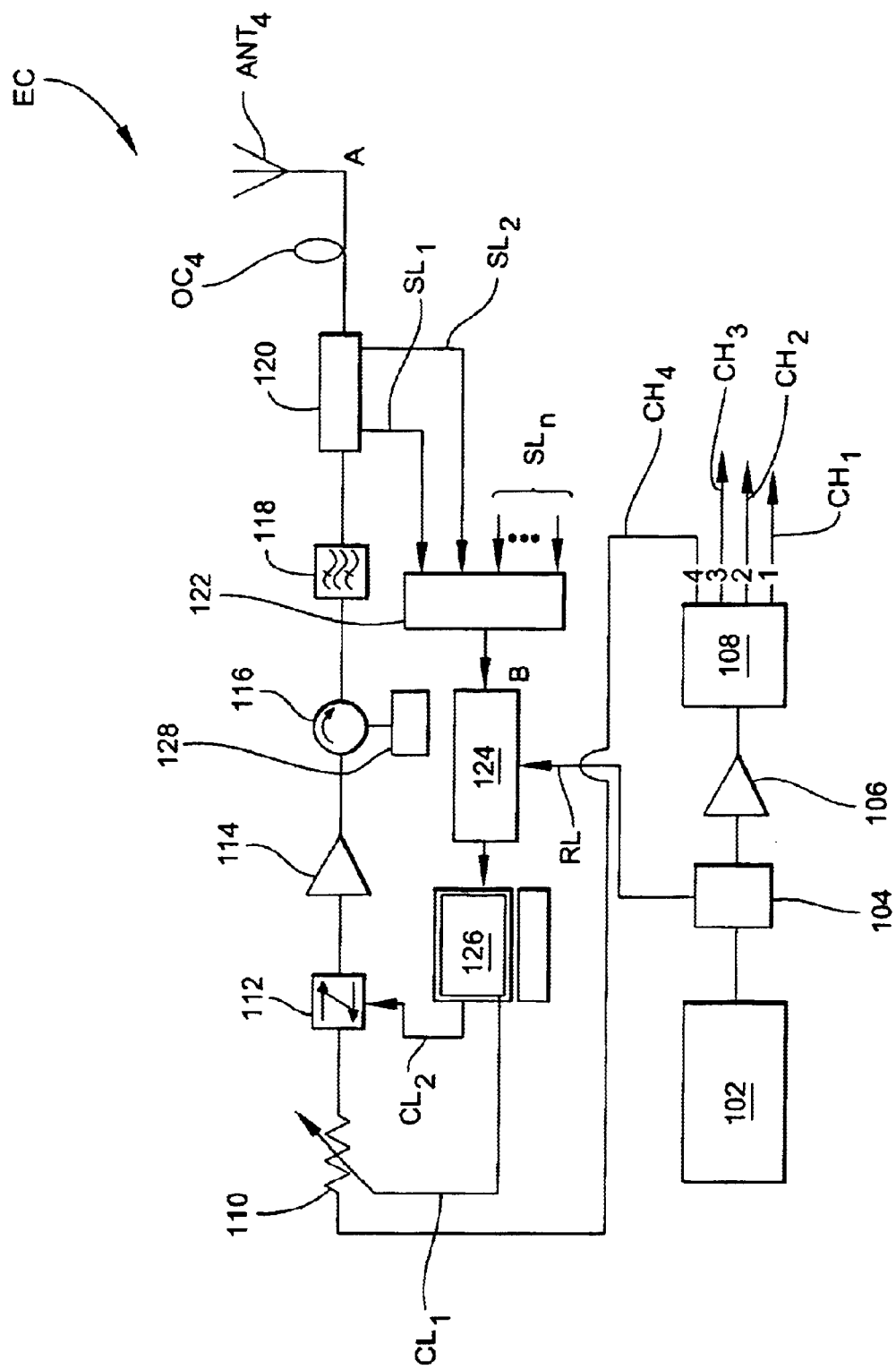
FIG. 8 is a schematic diagram of electrical circuitry provided with the hyperthermia treatment apparatus according to embodiments disclosed herein.

Referring now to FIG. 8, a block diagram depicts one exemplary embodiment of electrical circuitry EC suitable for driving antennas $ANT_1$–$ANT_4$ of hyperthermia treatment apparatus HTA (see, for example, FIGS. 1A and 1B). The primary functions of electrical circuitry EC are to generate RF signals at a desired frequency (e.g., approximately 130–160 MHz), and divide the power of the signals into separate channels $CH_1$–$CH_4$ for distribution to corresponding antennas $ANT_1$–$ANT_4$ provided with hyperthermia treatment apparatus HTA. In addition, advantageous embodiments of electrical circuitry EC enable, in each channel $CH_1$–$CH_4$, attenuation of the amplitude of the RF signal to control final output power in that channel $CH_1$–$CH_4$. Moreover, in at least some of the channels $CH_1$–$CH_4$, electrical circuitry EC enables variation of the phase of the RF signal to establish RF standing wave patterns in cavity 14 of hyperthermia treatment apparatus HTA that are optimal for the embodiment of hyperthermia treatment apparatus HTA being employed, the type of tissue being treated, the characteristics of the tumor afflicting the tissue, the status of the patient (e.g., pre-surgical, post-mastectomy, and the like), and the type of therapy that is to be enhanced by hyperthermia treatment apparatus HTA (e.g., chemotherapy, radiotherapy, and the like). In further embodiments, electrical circuitry EC provides closed loop control of amplitude and phase in each channel $CH_1$–$CH_4$ during a hyperthermia treatment procedure. In still further embodiments, electrical circuitry EC enables impedance matching to optimize the transfer of RF power to antennas $ANT_1$–$ANT_4$.

In the exemplary embodiment illustrated in FIG. 8, electrical circuitry EC comprises an RF signal generator 102 of any suitable type, one example being an HP 8647A signal generator available from Hewlett-Packard, Palo Alto, Calif. RF signal generator 102 generates the initial RF signal for the system. The initial signal is then split by a 2-way power divider 104 to provide a reference signal over a reference line RL for a purpose described hereinbelow. The main initial signal is then amplified by a pre-amp 106 and fed to a 4-way power divider 108. At 4-way power divider 108, the amplified signal is split into four channels $CH_1$–$CH_4$, although more or less channels could be provided.

It will be noted that, for brevity, FIG. 8 does not show all components associated with first, second and third channels $CH_1$–$CH_3$. However, the circuitry associated with first, second and third channels $CH_1$–$CH_3$ is similar to that of fourth channel $CH_4$. All channels $CH_1$–$CH_4$ can include an electronically variable attenuator 110. One primary difference in the present embodiment is that first channel $CH_1$ does not include an electronically variable phase shifter 112, whereas each of second, third and fourth channels $CH_2$–$CH_4$ include phase shifter 112.

Continuing with the illustrated example of fourth channel $CH_4$, the divided RF signal dedicated for fourth channel $CH_4$ is fed to variable attenuator 110, where the amplitude of the signal and thus the final output power of fourth channel $CH_4$ can be controlled. The output phase of fourth channel $CH_4$ is controlled by phase shifter 112. After the phase and amplitude of the signal have been set, a high-power amplifier 114 amplifies the signal up to a maximum power of, for example, 160 W. One example of a suitable high-power amplifier 114 is available from LCF Enterprises, Post Falls, Id. Once the signal has been appropriately conditioned, it is transmitted over a length of low-loss output cable $OC_4$ to fourth antenna $ANT_4$ from which it is outputted into cavity 14 of treatment applicator TA (see, for example, FIG. 2C).

Referring again to FIG. 8, electronic circuitry EC can include a circulator 116 positioned after high-power amplifier 114 to isolate high-power amplifier 114 from the rest of fourth channel $CH_4$ and allow high-power amplifier 114 to operate reliably under any loading condition. Circulator 116 is particularly useful in clinical applications, because the loading condition of antennas $ANT_1$–$ANT_4$ varies from one treatment to another and can lead to impedance mismatch. In addition, a high-pass filter 118 can be provided to filter the signal at a desired cut-off frequency. In the present example, the bandwidth of the system ranges from approximately 100–200 MHz, although the actual bandwidth might be narrower due to the use of circulator 116 and high-pass filter 118. The RF frequency should be low enough to ensure sufficiently deep penetration into tissue where a tumor is located, as opposed to other frequency ranges such as microwaves that are considered herein to propagate at too high of a frequency to offer suitable penetration.

Electronic circuitry EC also includes a closed loop feedback circuit for monitoring and adjusting amplitude and phase during operation. At the output of fourth channel $CH_4$, a dual directional coupler 120 taps off a portion of the forward power and reflected power in output cable $OC_4$ and feeds these sample signals to a switch 122 via respective sample lines $SL_1$–$SL_2$. An example of a suitable dual directional coupler 120 is available from Bird Electronic, Solon, Ohio. The respective dual directional couplers 120 of other channels $CH_1$–$CH_4$ also provide sample signals to switch 122, as indicated by additional sample lines $SL_n$. Switch 122 connects a selected channel $CH_1$–$CH_4$ to a vector voltmeter 124, which measures the amplitude and phase of the channel $CH_1$–$CH_4$ being sampled. Switch 122 can be controlled to cycle or scan through all of channels $CH_1$–$CH_4$ so that phase and amplitude measurements for all channels $CH_1$–$CH_4$ are read from vector voltmeter 124 by a computer 126 several times per second. An example of a suitable computer 126 is a DELL® Model No. XP120C PC computer. Computer 126 receives the measurements made by vector voltmeter 124 as inputs for a software algorithm executable by the central processing unit (CPU) of computer 126. The algorithm compares these measurements to predetermined set points and makes appropriate adjustments by sending control signals over control signal lines $CL_1$ and $CL_2$ to variable attenuator 110 and phase shifter 112, respectively.

The phase measurements for all channels $CH_1$–$CH_4$ should be made with respect to the same reference signal. First channel $CH_1$ is arbitrarily selected in the present embodiment to be the reference channel of the system, since its phase is always zero and does not require a phase shifter 112. Hence, first channel $CH_1$ would be the logical choice for providing the reference input to vector voltmeter 124. However, for some treatments, first channel $CH_1$ might be turned off and therefore inactive. To ensure that vector voltmeter 124 can make measurements under this circumstance, a portion of the signal from RF signal generator 102 (which is always ON during treatment) is routed by 2-way power divider 104 to vector voltmeter 124 over reference line RL, prior to the main signal being divided into channels $CH_1$–$CH_4$ at 4-way power divider 108.

The RF power system provided by electrical circuitry EC can be calibrated to enable vector voltmeter 124 to accurately measure signals sampled from each channel $CH_1$–$CH_4$. It can be seen from FIG. 8 that while samples are measured at point B corresponding to the selected input to vector voltmeter 124 from switch 122, the phase and amplitude of the RF signal are of greater interest at point A, where output cable $OC_4$ attaches to antenna $ANT_4$. To calibrate each channel $CH_1$–$CH_4$, the input of dual directional coupler 120 can be connected to any signal generator, and point A of output cable $OC_4$, which usually is connected to antenna $ANT_4$, can then be connected to the reference signal port of vector voltmeter 124 in place of reference line RL, thus becoming the reference signal for vector voltmeter 124. Vector voltmeter 124 then measures the difference in phase and amplitude between point A and point B over a band of frequencies. When the system is reconnected in the standard operating configuration shown in FIG. 8, computer 126 can retrieve the values measured during calibration and add them to the vector voltmeter 124 readings at point B to reconstruct the amplitude and phase values at point A. This process can be implemented by software executed in computer 126.

To increase the efficiency of power transfer from the RF energy source to antennas $ANT_1$–$ANT_4$, electrical circuitry EC can provide for impedance matching. As appreciated by persons skilled in the art, the amount of power radiated from antennas $ANT_1$–$ANT_4$ is frequency-dependent. If the impedance of any given antenna $ANT_1$–$ANT_4$ is not close to that of its corresponding output cable $OC_1$–$OC_4$, which typically is a 50-Ohm impedance, there will be an impedance mismatch and much of the RF energy sent to that antenna $ANT_1$–$ANT_4$ will be reflected back into the system where it is absorbed by a dummy load 128. The input impedance of any given antenna $ANT_1$–$ANT_4$ depends on the material and the geometry of the load placed inside treatment applicator TA. Since the load changes from treatment to treatment, it is not always possible to know what frequency provides the best impedance match. This problem can be solved by scanning each individual channel $CH_1$–$CH_4$ across the usable bandwidth of the system and recording the impedance match (i.e., the ratio of reflected power to forward power) at each frequency. While channels $CH_1$–$CH_4$ all match at similar frequencies, they do not match at exactly the same frequency. The match of the entire system at each frequency is taken to be the match of the worst channel at that frequency. It is then suggested that the therapist use the frequency at which the entire system has the best match.

During treatment, it is possible for the impedance to change due to, for example, patient movement. As a result, it is possible for the impedance match of the system to change during treatment. A matching algorithm, which can be implemented by software executed by computer 126, can be run at any point during a treatment to determine if it would be advantageous to change frequencies. Inputs for the matching algorithm include the frequency setting of RF signal generator 102, the power setting for the amplifier of each channel $CH_1$–$CH_4$ (e.g., high-power amplifier 114 of fourth channel $CH_4$), and the phase setting for each channel $CH_1$–$CH_4$. For each channel $CH_1$–$CH_4$, computer 126 can display the forward power, reverse power, and phase measured by vector voltmeter 124, as well as amplifier current. Vector voltmeter 124 samples phase, forward power, and reverse power in each channel $CH_1$–$CH_4$ at some interval (e.g., twenty times per second), makes a comparison with the respective set values, and adjusts the respective voltages over control signal lines $CL_1$ and $CL_2$ (e.g., 0–5 V) to control variable attenuator 110 and variable phase shifter 112 associated with each channel $CH_1$–$CH_4$.

It thus can be seen that electrical circuitry EC provides a 4-channel RF power source for treatment applicator TA (FIGS. 1–7), with seven degrees of freedom or adjustability (four power settings ranging from approximately 0–160 W, three relative phase settings ranging from approximately +/−180 degrees). If, in the present example, all four channels $CH_1$–$CH_4$ are operating at full power, the system can deliver a total output of 640 W.

It can be appreciated by persons skilled in the art that while electronic circuitry EC illustrated by way of example in FIG. 8 is configured to drive the four-antenna embodiment of treatment applicator TA (FIGS. 2A–3), electronic circuitry EC can be modified, or similar circuitry provided, so as to accommodate any of the other embodiments of treatment applicator TA (for example, FIGS. 4–7). For instance, when using the five-antenna embodiment of treatment applicator TA (FIG. 4), the output of fourth channel $CH_4$ could be split using a coaxial 2-way splitter to drive two antennas $ANT_4$ and $ANT_5$ (FIG. 4) instead of one.

It can be further appreciated by persons skilled in the art that the algorithms described hereinabove can be implemented by any suitable software written in an appropriate language such as Visual Basic, C++, or the like.

In operation, hyperthermia treatment apparatus HTA (see generally FIGS. 1A–8) can be employed to heat any material that can benefit from the application of coherently focused RF energy coupled from a phased antenna array and through a medium such as deionized water. As described hereinabove, hyperthermia treatment apparatus HTA is particularly advantageous for the treatment of locally advanced or inflammatory breast cancer in presurgical patients, and of the recurrence of chest wall diseases in post-mastectomy patients. Depending on the nature of the tissue and tumor contained therein to be treated, the configuration of treatment applicator TA is selected—e.g., whether to use the four, five, six, or other multiple antenna embodiment of treatment applicator TA, whether to use tissue support structure 30 (see, for example, FIGS. 3, 4, 6 and 7), and whether container 32 (FIGS. 3 and 4) or pillow 62 (FIGS. 6 and 7) is used as tissue support structure 30.

Once treatment applicator TA has been selected, the channels $CH_1$–$CH_4$ of electrical circuitry EC that are to be active are selected, as well as the desired settings (e.g., amplitude and phase) for the RF signals to be carried in each active channel $CH_1$–$CH_4$. In addition, the frequency setting of RF signal generator 102 is selected. These various settings are selected so as to provide a beneficial standing RF wave pattern in cavity 14 of treatment applicator TA that is tailored, for example, to the configuration chosen for treatment applicator TA. Software executed by computer 126 (FIG. 8) can be provided to assist in this optimization. The patient is then positioned on patient support structure 20 (FIGS. 1A and 1B) with the tumor-containing tissue supported on or in treatment applicator TA as described hereinabove. In general, the tissue can be characterized as being in operative alignment with antennas ANT, meaning that the tissue is either immersed in cavity 14 or supported over or in close proximity to cavity 14 as appropriate to effect electromagnetic coupling and direct RF standing waves to the tumor. Electrical circuitry EC is then operated as described above to supply RF energy to treatment applicator TA, and antennas ANT broadcast the RF energy through cavity 14 to the tumor-containing tissue whereby the tumor is heated. In addition, treatment applicator TA is preferably connected with temperature regulation device TRD (FIG. 1B) to circulate fluid F such as deionized water through cavity 14 at a temperature setting comfortable for the patient. The hyperthermia procedure proceeds in this manner for a predetermined schedule (e.g., one hour per cycle, one cycle every three weeks, four cycles total).

Hyperthermia treatment apparatus HTA is particularly advantageous as a mechanism for enhancing tumor-related therapeutic procedures provided for cancer patients. It is contemplated that the therapeutic procedure will typically be carried out prior to the use of hyperthermia treatment apparatus HTA, but the practice of the embodiments disclosed herein is not limited to the order in which tumor-related therapy and hyperthermia treatment are performed. One example is radiotherapy, the effects of which have been proven to be improved through the application of heat to the tumor being treated. Another example is chemotherapy.

In particular, certain types of chemotherapy are administered to patients in liposomal encapsulations or coatings. When treatment applicator TA is employed to focus RF energy at the tumor of a patient, the consequent heating of the tissue can have a number of benefits. Heating promotes the disintegration of the chemotherapy-carrying liposomes. Heating draws liposomes out of the bloodstream and directly to the site of the tumor, thus concentrating the chemotherapy-containing liposomes where they are most needed. A tumor's blood vessels are much more leaky or chaotic than normal blood vessels. Heating pulls the blood vessels apart more than usual, thereby allowing the liposomes to leak out and pool into the tumor's interstitial spaces. Consequently, the chemotherapy is preferentially delivered to the tumor and not to surrounding tissue. In normal tissues of the patient's body that remain unheated during the hyperthermia treatment, the chemotherapy slowly leaks out from the liposomes over a period of typically three or four weeks, a rate sufficient to enable the liver and spleen of the patient to blunt any toxic side effects. Moreover, the heat provided by hyperthermia as disclosed herein increases the rate of the chemotherapy's uptake into the cancer cell itself. Heating further increases oxygen levels within the tumor, which is advantageous for many chemotherapy agents whose proper functioning critically relies on oxygen. Heating also boosts the potency of the chemotherapy by interfering with mechanisms that control a cancer cell's ability to replicate. Finally, heating amplifies the level of DNA damage that chemotherapy inflicts upon the cancer cell by inhibiting enzymes that normally repair such DNA damage.

Presently, "melting" liposomes are being developed that melt quickly in response to heating, thereby dumping their contents directly into a tumor within about twenty seconds of heating. Some of these liposomes have a precisely determined melting point such as about 40° C. (104° F.). The effects of chemotherapy encapsulated in such liposomes can be advantageously enhanced by performing hyperthermia treatment according to the embodiments disclosed herein. For instance, referring to FIGS. 1A and 1B, the bath of fluid F circulated in cavity 14 of treatment applicator TA can be maintained by temperature regulating device at 40° C., which is warm enough to engage the benefits of heating but cool enough to prevent burning the skin of the patient.

Data have been acquired from pre-clinical and phase I clinical studies on human patients undergoing hyperthermia treatment using hyperthermia treatment apparatus HTA in conjunction with chemotherapy infusion via liposomes. In particular, twenty-one women afflicted with newly diagnosed breast cancers participated in a twelve-week hyperthermia trial. It was found that encapsulating the chemotherapy inside of liposomes enabled the delivery of thirty times more chemotherapy to the tumor site as compared with more conventional techniques, and without poisoning the rest of the body. Patients generally experienced less nausea, fatigue, and cardiac toxicity than with traditional chemotherapy. In addition, the results showed that the combined therapy halted tumor growth in all patients and at least shrunk tumors in half of the patients. Eleven percent of the patients had complete pathologic responses, meaning no cancer was found in the breast tissue upon analyzing its surgical remains. Thirty-three percent of patients had complete clinical responses, meaning visible signs of the tumor could no longer be detected. Seventeen percent of patients were converted from mastectomy candidates to lumpectomy candidates.

As one non-limiting example of a combined therapy/hyperthermia treatment, a traditional cancer therapy (e.g., chemotherapy and/or radiation) is given to a patient and followed by a CT or other appropriate scanning technique to locate the precise location of the tumor within the tissue. The hyperthermia treatment is then given as described hereinabove. After the final hyperthermia treatment is given, a radiation oncologist measures the tumor shrinkage by any suitable means, and recommends the least invasive type of surgery to remove the tumor. Surgery is followed by additional therapy and hyperthermia treatment, if one or both procedures are indicated at this stage, to kill any undetected cancer cells in the tissue.

In the traditional order of cancer therapy, surgery is performed first and chemotherapy and radiation performed last. It can be seen from the foregoing disclosure that the methods disclosed herein can be characterized as reversing that traditional order. Hyperthermia treatment apparatus HTA can be implemented as part of a more recent therapeutic model termed "neo-adjuvant" therapy, meaning the treatment occurs prior to surgery. In many cases, neo-adjuvant therapy is a more logical sequence of treatment events, because it requires less invasive surgery and offers patients a wider range of treatment-related options. Moreover, the methods disclosed herein can further the treatment goal of shrinking tumors enough for surgeons to successfully remove them without damaging the surrounding tissue or leaving behind errant cancer cells.

It can be appreciated that the embodiments disclosed hereinabove have potential applications outside the immediate scope of cancer therapy, such as cellular necrosis, chemical reaction kinetics, and catalysis.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. An apparatus for providing hyperthermia treatment to the chest region for enhancing cancer therapy, comprising:
   (a) an applicator body having an inner surface extending from an aperture and having an at least generally concave lower portion and defining an open cavity for receiving RF standing waves; and
   (b) a plurality of antennas operatively associated with the applicator body and arrayed for transmitting RF standing waves at respective selected amplitudes and relative phases into the cavity and generally toward a tumor-containing tissue disposed in operative alignment with the antennas.

2. The apparatus according to claim 1 wherein the body comprises a plurality of body sections, and the plurality of antennas are mounted to one or more of the body sections.

3. The apparatus according to claim 2 wherein the body comprises six body sections, the plurality of antennas comprise four antennas, and each antenna is mounted to one of the six body sections.

4. The apparatus according to claim 3 wherein the six body sections comprise four side sections defining the aperture and two bottom sections, two of the side sections are disposed in opposing spaced relation and are generally perpendicular to the aperture, and the other two side sections are disposed in opposing spaced relation and are angled relative to the aperture.

5. The apparatus according to claim 4 wherein each antenna is mounted to a respective one of the two angled side sections and two bottom sections.

6. The apparatus according to claim 5 comprising an additional two antennas, each of the additional two antennas mounted to a respective perpendicular side section.

7. The apparatus according to claim 2 wherein the body comprises five body sections, the plurality of antennas comprises five antennas, and each antenna is mounted to a corresponding body section.

8. The apparatus according to claim 7 wherein the five body sections comprise four side sections defining the aperture and one bottom section, two of the side sections are spaced in opposing spaced relation and are generally perpendicular to the aperture, and the two other side sections are disposed in opposing spaced relation and are angled relative to the aperture.

9. The apparatus according to claim 1 wherein each antenna comprises a generally symmetrical arrangement of two antenna elements.

10. The apparatus according to claim 9 wherein each antenna element is generally C-shaped and opens away from the other antenna element.

11. The apparatus according to claim 10 wherein each antenna is bowtie-shaped.

12. The apparatus according to claim 1 comprising a tissue support mounted at the aperture for supporting tissue in operative alignment with the antennas.

13. The apparatus according to claim 12 wherein the tissue support comprises a temperature-sensing device.

14. The apparatus according to claim 13 wherein the temperature-sensing device is a magnetic coil mounted to the tissue support for communicating with an MRI device.

15. The apparatus according to claim 12 wherein the tissue support comprises an open container extending into the cavity for supporting tissue therein.

16. The apparatus according to claim 12 wherein the tissue support comprises a fluid-filled pillow for supporting tissue thereon.

17. The apparatus according to claim 1 comprising a patient support suitable for supporting a patient during hyperthermia treatment, wherein the applicator body is mounted to the patient support.

18. The apparatus according to claim 1 comprising a temperature regulation device communicating with the cavity for circulating a temperature regulated fluid therethrough.

19. The apparatus according to claim 1 wherein the body includes an inlet and an outlet fluidly communicating with the cavity for circulating a fluid therethrough.

20. The apparatus according to claim 1 comprising an RF signal generator communicating with the antennas.

21. The apparatus according to claim 20 comprising a variable attenuator interconnected between the RF signal generator and the antennas for controlling respective amplitudes of RF signals received by one or more of the antennas.

22. The apparatus according to claim 20 comprising a variable phase shifter interconnected between the RF signal generator and the antennas for controlling respective phases of RF signals received by one or more of the antennas.

23. The apparatus according to claim 20 comprising a power divider interconnected between the RF signal generator and the antennas for dividing an RF signal generated by the RF signal generator into a plurality of channels corresponding to the array of antennas.

24. The apparatus according to claim 23 comprising a device selectively communicating by one or more of the channels for measuring an amplitude and/or phase of a channel signal carried in a selected channel.

25. A method for providing hyperthermia treatment to the chest region for enhancing cancer therapy, comprising the steps of:
   (a) placing a tumor-containing tissue in operative alignment with a phased array of antennas operatively associated with a body having an inner surface extending from an aperture and having an at least generally concave lower portion defining a cavity containing a fluid; and
   (b) transmitting RF energy from the antennas through the fluid and to the tissue to heat the tissue.

26. The method according to claim 25 comprising the step of monitoring a temperature of the tissue.

27. The method according to claim 26 wherein monitoring comprises inserting a temperature-sensing device into the tissue.

28. The method according to claim 27 wherein monitoring comprises inserting a catheter into the tissue and inserting the temperature-sensing device into the catheter.

29. The method according to claim 26 wherein monitoring comprises using a magnetic coil surrounding the tissue and coupled to an MRI device.

30. The method according to claim 25 wherein the fluid contained in the cavity is deionized water.

31. The method according to claim 25 wherein placing in operative alignment comprises supporting the tissue with a fluid-containing support mounted at the cavity.

32. The method according to claim 31 comprising the steps of selecting a type of the support based on the type of tissue to be treated, and mounting the selected support at the cavity.

33. The method according to claim 31 wherein placing in operative alignment comprises immersing the tissue in a fluid-filled container extending into the cavity.

34. The method according to claim 33 comprising the steps of selecting a size of the container based on the size of the tissue to be treated, and mounting the selected container to the cavity.

35. The method according to claim 31 wherein supporting comprises positioning the tissue on a fluid-filled pillow.

36. The method according to claim 25 comprising transmitting RF signals to each of the antennas at a desired frequency.

37. The method according to claim 36 wherein the frequency ranges from approximately 130 to approximately 160 MHz.

38. The method according to claim 25 comprising controlling respective amplitudes of RF signals outputted to one or more of the antennas.

39. The method according to claim 25 comprising controlling respective phases of RF signals outputted to one or more of the antennas.

40. The method according to claim 25 wherein the tissue is a tumor-containing breast of a patient.

41. The method according to claim 25 wherein the tissue is a tumor-containing chest wall of a patient.

42. A method for providing hyperthermia treatment to the chest region to enhance tumor-related therapy, comprising the steps of:
   (a) treating a tumor-containing tissue by performing a tumor-related therapeutical procedure;
   (b) placing the tissue in an operative alignment with a phased array of antennas operatively associated with a body having an inner surface extending from an aperture and having an at least generally concave lower portion defining a cavity containing a fluid; and
   (c) transfixing RF energy from the antennas, through the fluid and into the tissue to heat the tissue.

43. The method according to claim 42 wherein placing in operative alignment comprises supporting the tissue with a fluid-containing support mounted at the cavity.

44. The method according to claim 43 wherein supporting comprises immersing the tissue in a fluid-filled container extending into the cavity.

45. The method according to claim 43 wherein supporting comprises positioning the tissue on a fluid-filled pillow.

46. The method according to claim 42 wherein the tissue is a tumor-containing breast of a patient.

47. The method according to claim 42 wherein the tissue is a tumor-containing chest wall of a patient.

48. The method according to claim 42 wherein treating the tissue comprises providing chemotherapy.

49. The method according to claim 48 wherein providing chemotherapy comprising administering liposomes containing the chemotherapy.

50. The method according to claim 42 wherein treating the tissue comprises providing radiotherapy.

51. An apparatus for providing hyperthermia treatment for enhancing cancer therapy, comprising:
   (a) an applicator body having a concave profile extending from an aperture, wherein the body comprises six body sections and defines an open cavity for receiving RF standing waves; and
   (b) a plurality of four antennas, each antenna mounted to a respective one of the six body sections, and wherein the plurality of antennas are arrayed for transmitting RF standing waves at respective selected amplitudes and relative phases into the cavity and generally toward a tumor-containing tissue disposed in operative alignment with the antennas.

52. The apparatus according to claim 51 wherein the six body sections comprise four side sections defining the aperture and two bottom sections, two of the side sections are disposed in opposing spaced relation and are generally perpendicular to the aperture, and the other two side sections are disposed in opposing spaced relation and are angled relative to the aperture.

53. The apparatus according to claim 52 wherein each antenna is mounted to a respective one of the two angled side sections and two bottom sections.

54. The apparatus according to claim 53 comprising an additional two antennas, each of the additional two antennas mounted to a respective perpendicular side section.

55. An apparatus for providing hyperthermia treatment for enhancing cancer therapy, comprising:
   (a) an applicator body having a concave profile extending from an aperture, wherein the body comprises five body sections and defines an open cavity for receiving RF standing waves; and
   (b) a plurality of five antennas, each antenna mounted to a corresponding body section, and wherein the plurality of antennas are arrayed for transmitting RF standing waves at respective selected amplitudes and relative phases into the cavity and generally toward a tumor-containing tissue disposed in operative alignment with the antennas.

56. The apparatus according to claim 55 wherein the five body sections comprise four side sections defining the aperture and one bottom section, two of the side sections are spaced in opposing spaced relation and are generally perpendicular to the aperture, and the two other side sections are disposed in opposing spaced relation and are angled relative to the aperture.

57. An apparatus for providing hyperthermia treatment for enhancing cancer therapy, comprising:
   (a) an applicator body having a concave profile extending from an aperture and defining an open cavity for receiving RF standing waves;
   (b) a plurality of antennas operatively associated with the applicator body and arrayed for transmitting RF standing waves at respective selected amplitudes and relative phases into the cavity and generally toward a tumor-containing tissue disposed in operative alignment with the antennas; and
   (c) a tissue support mounted at the aperture for supporting the tissue in operative alignment with the antennas wherein the tissue support comprises a temperature-sensing device comprising a magnetic coil mounted to the tissue support for communicating with an MRI device.

58. An apparatus for providing hyperthermia treatment for enhancing cancer therapy, comprising:
   (a) an applicator body having a concave profile extending from an aperture and defining an open cavity for receiving RF standing waves;
   (b) a plurality of antennas operatively associated with the applicator body and arrayed for transmitting RF standing waves at respective selected amplitudes and relative phases into the cavity and generally toward a tumor-containing tissue disposed in operative alignment with the antennas; and
   (c) a tissue support mounted at the aperture for supporting the tissue in operative alignment with the antennas wherein the tissue support comprises an open container extending into the cavity for supporting tissue therein.

59. A method for providing hyperthermia treatment for enhancing cancer therapy, comprising the steps of:
   (a) placing a tumor-containing tissue in operative alignment with a phased array of antennas operatively associated with a body defining a cavity containing a fluid;
   (b) transmitting RF energy from the antennas through the fluid and to the tissue to heat the tissue; and
   (c) monitoring a temperature of the tissue using a magnetic coil surrounding the tissue and coupled to an MRI device.

60. A method for providing hyperthermia treatment for enhancing cancer therapy, comprising the steps of:
   (a) placing a tumor-containing tissue in operative alignment with a phased array of antennas operatively associated with a body defining a cavity containing a fluid wherein the placing in operative alignment comprises supporting the tissue with a fluid-containing support mounted at the cavity and immersing the tissue in a fluid-filled container extending into the cavity; and
   (b) transmitting RF energy from the antennas through the fluid and to the tissue to heat the tissue.

61. The method according to claim 60 comprising the steps of selecting a size of the container based on the size of the tissue to be treated, and mounting the selected container to the cavity.

* * * * *